Figure 1:
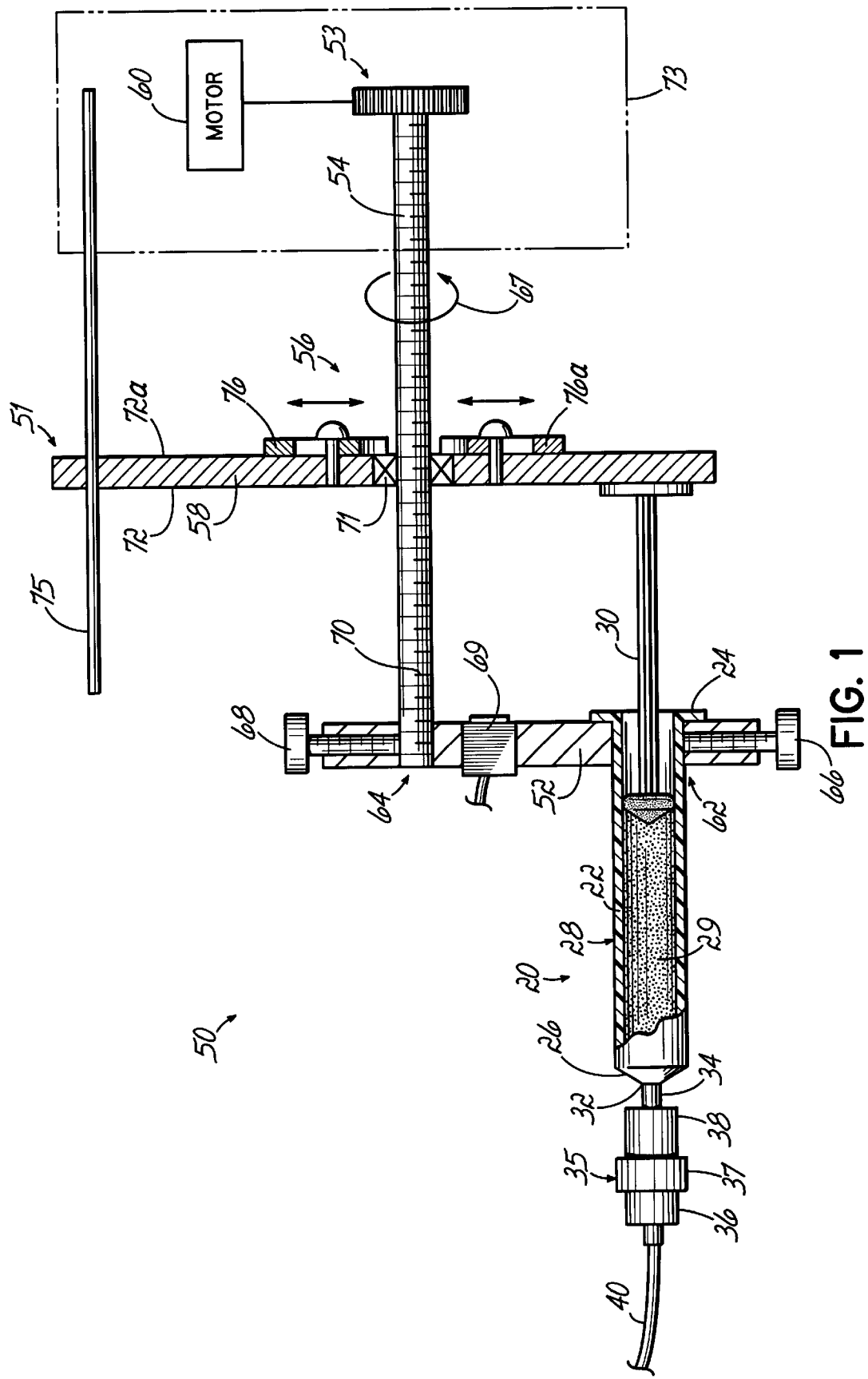

US006387077B1

(12) United States Patent
Klibanov et al.

(10) Patent No.: US 6,387,077 B1
(45) Date of Patent: May 14, 2002

(54) APPARATUS AND METHOD FOR PROVIDING A SUSPENDED AGENT

(75) Inventors: Alexander Lazarevich Klibanov, St. Louis; Ronald Walter Hagen; Mark Edward Boyce, both of St. Charles, all of MO (US)

(73) Assignee: Mallinckrodt Inc., St. Louis, MO (US)

( * ) Notice: Subject to any disclaimer, the term of this patent is extended or adjusted under 35 U.S.C. 154(b) by 61 days.

(21) Appl. No.: 09/687,323

(22) Filed: Oct. 13, 2000

(51) Int. Cl.[7] .................................................. A61M 5/00

(52) U.S. Cl. ........................ 604/181; 604/154; 604/155; 128/DIG. 1

(58) Field of Search ................................ 604/181, 154, 604/155, 208, 209, 211; 222/309, 311; 128/DIG. 1, DIG. 12, DIG. 13

(56) References Cited

U.S. PATENT DOCUMENTS

| | | | | | |
|---|---|---|---|---|---|
| 2,734,504 | A | | 2/1956 | Crescas et al. | 128/218 |
| 3,415,419 | A | | 12/1968 | Jewett et al. | 222/76 |
| 3,720,211 | A | * | 3/1973 | Kyrias | 604/155 |
| 4,191,187 | A | | 3/1980 | Wright | 128/218 |
| 4,424,720 | A | * | 1/1984 | Bucchianeri | 128/DIG. 1 |
| 4,465,475 | A | | 8/1984 | Mardorf et al. | 604/155 |
| 4,475,666 | A | * | 10/1984 | Bilbrey et al. | 604/155 |
| 4,560,979 | A | * | 12/1985 | Rosskopf | 128/DIG. 1 |
| 4,648,872 | A | | 3/1987 | Kamen | 604/155 |
| 4,668,220 | A | * | 5/1987 | Hawrylenko | 604/155 |
| 4,676,122 | A | * | 6/1987 | Szabo et al. | 604/154 |
| 4,731,058 | A | | 3/1988 | Doan | 604/155 |
| 4,749,109 | A | | 6/1988 | Kamen | 604/155 |
| 4,769,009 | A | * | 9/1988 | Dykstra | 604/155 |
| 4,931,041 | A | * | 6/1990 | Faeser | 604/155 |
| 4,952,205 | A | | 8/1990 | Mauerer et al. | 604/67 |
| 5,006,112 | A | | 4/1991 | Metzner | 604/155 |
| 5,034,004 | A | * | 7/1991 | Crankshaw | 604/154 |
| 5,176,646 | A | * | 1/1993 | Kuroda | 604/154 |
| 5,219,099 | A | * | 6/1993 | Spence et al. | 604/155 |
| 5,244,461 | A | * | 9/1993 | Derlien | 604/154 |
| 5,279,569 | A | | 1/1994 | Neer et al. | 604/154 |
| 5,456,670 | A | | 10/1995 | Neer et al. | 604/155 |

FOREIGN PATENT DOCUMENTS

| | | | |
|---|---|---|---|
| WO | WO 96/18420 | 6/1996 | A61K/49/00 |
| WO | WO 99/27981 | 6/1999 | A61M/5/145 |

* cited by examiner

*Primary Examiner*—Teresa Walberg
*Assistant Examiner*—Fadi H. Dahbour
(74) *Attorney, Agent, or Firm*—Wood, Herron & Evans, L.L.P.

(57) ABSTRACT

Apparatus and methods for maintaining the suspension of an agent suspended in a suspending medium in which a container holding the agent is revolved about an axis to create and maintain the suspension and the agent is selectively provided from the container. The agent may be selectively provided from the container while the container is simultaneously or intermittently revolved in a planetary orbit about an axis of rotation generally parallel to an axis of the container for maintaining the suspension. Alternatively, the container may be rotated about its longitudinal axis by a source of rotation to create and maintain the suspension while the agent is provided from the container due to a force imparted by the source of rotation.

30 Claims, 3 Drawing Sheets

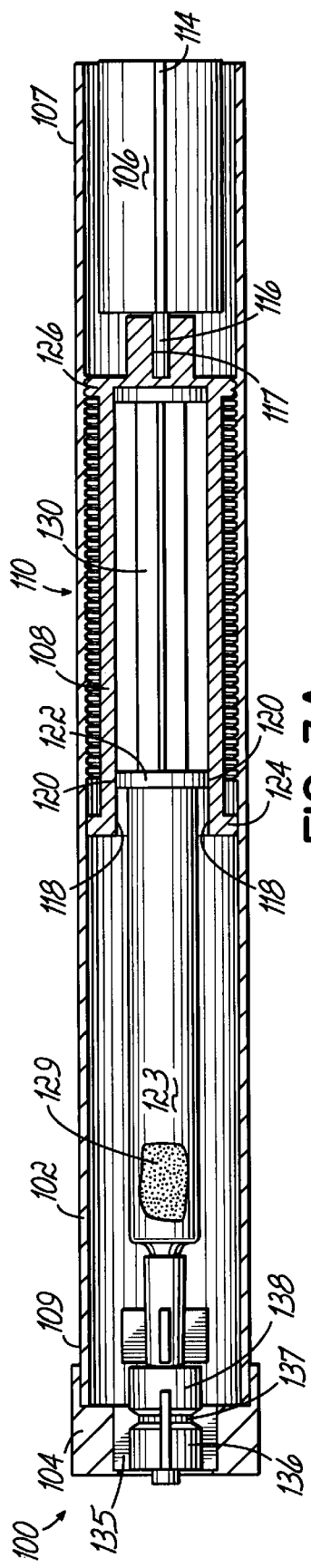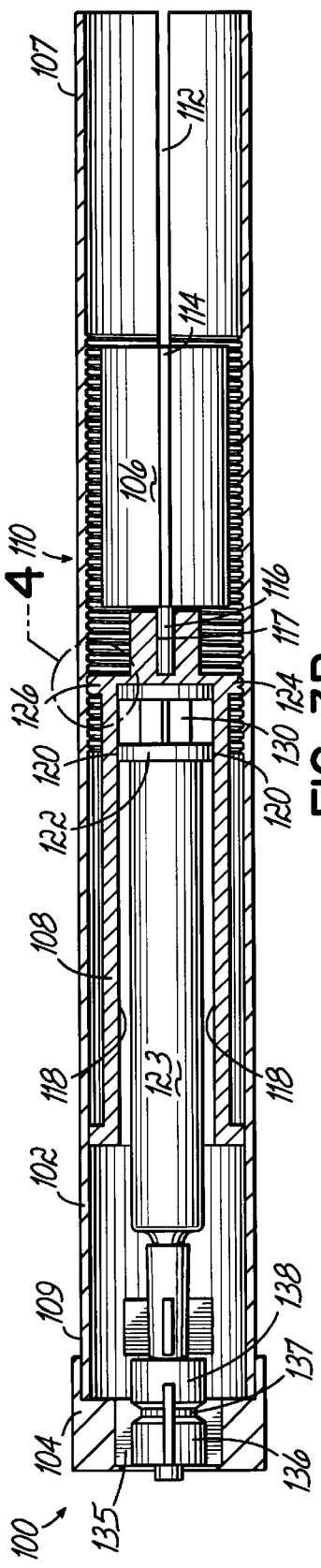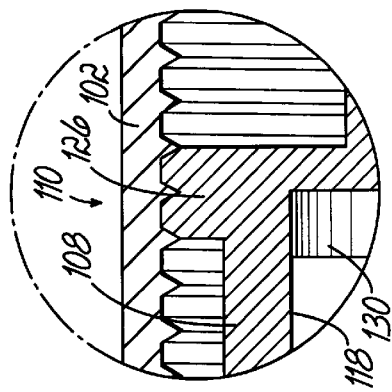
FIG. 3A
FIG. 3B
FIG. 4

APPARATUS AND METHOD FOR PROVIDING A SUSPENDED AGENT

FIELD OF THE INVENTION

The present invention relates to an apparatus and method for providing a homogeneous suspension of an agent in a suspending medium.

BACKGROUND OF THE INVENTION

A suspension is a mixture of fine, non-settling particles of any solid within a liquid or gas suspending medium. The particles are referred to as the dispersed phase, and the suspending medium is referred to as the continuous phase. The fine particles tend to persist in a suspended state go long as dissipative forces that encourage accumulation are overcome or compensated for. When the compensation becomes inadequate due to, for example, buoyancy, gravity acting on agglomerated macroparticles, or the nonconservative forces of fluid viscosity, particle motion is no longer energetic enough to resist the acting forces within a stationary container, and the particles will accumulate in various forms, such as agglomerates, clumps, sediments, and the like. Once particles accumulate in one of these forms, they must be resuspended within the suspending medium by agitation.

One example of a suspension is a biomedical contrast imaging agent. Contrast agents may contain particles suspended in a pharmaceutically acceptable liquid suspending carrier medium. When injected into the vascular system of a patient, the contrast agent is transported in the bloodstream from the injection site to reach the targeted tissue or organ to be imaged. The agent provides contrast at the target site for enhancement of the resulting image. Imaging techniques used for medical diagnosis and therapy frequently rely upon contrast agents to enhance the quality of the images acquired.

The image enhancement value of a contrast agent is improved if the contrast agent is delivered to a patient at a controlled rate to produce an optimum concentration in the targeted tissue or organ for the specific imaging period. The dose must be sufficient to maintain a concentration of contrast agent in the targeted tissue or organ within the effective range for the minimum period to complete the imaging procedure. These parameters require accurate and precise dosing. Frequently, excess contrast agent is administered to ensure an adequate concentration at the target site.

Contrast agents may be administered relatively rapidly and over a relatively short period of time as a bolus injection, or over a relatively longer period of time and at a slower rate as an infusion. There are several advantages of infusion of contrast agent versus a bolus injection: perfusion studies may be performed over an extended time to visualize the flow of blood in an organ or specific tissue, the duration of the diagnostic imaging procedure may be extended, and elevated concentrations of contrast agent in the blood of the targeted tissue are avoided so that the image will not be overly attenuated. The disadvantages of infusion, however, are that the patient is receiving contrast agent over a longer time period, during which the agent may come out of suspension. This necessitates resuspension of agent during the imaging procedure.

Contrast agents may be administered by infusion using various types of devices. A conventional syringe may be used to inject contrast agent either manually or using an automated injector. A power injector may also be used, where a motor-driven plunger drive slowly and continuously advances the plunger of a syringe to incrementally dispense the syringe contents over an extended time and according to predetermined injection parameters such as flow rate, volume, duration, and time. Power injectors are commonly used for infusions since they provide greater reliability and consistency in infusion rate and dosage when compared to manual injectors.

A primary disadvantage of delivering a contrast agent suspension with a conventional syringe or a conventional power injector, however, is that the contrast agent may not remain homogeneously suspended over the duration of the infusion. As a result, contrast agent dispensed at or near the end of the infusion may have a different composition and/or density, compared with the contrast agent dispensed at or near the beginning of the infusion. The resulting image may contain artifacts due to non-uniform delivery of agent, which may result in misleading or inaccurate images. If the image quality is not suitable for its intended purpose, the entire imaging procedure may have to be repeated with additional cost, patient inconvenience, patient risk, and unnecessary utilization of facility resources.

One solution to this problem is to continuously agitate the contrast agent dispensed using a power injector. This may be accomplished by placing an agitation source, such as a magnetic stir bar, within a syringe barrel containing the suspended contrast agent and activating the stir bar by a coupled magnetic stir plate adjacent to the syringe. Another solution is to interrupt the injection, remove the syringe from the power injector, and manually agitate the contents. Yet another solution is to modify a conventional power injector to allow planetary revolution of the syringe about a longitudinal axis during injection.

These solutions are less than satisfactory. Such devices may be bulky and/or intricate, and may be difficult to use and accommodate in an area where imaging is to be performed. A modified power injector may not comply with existing syringe standards, requiring the use of customized, non-standard syringes. The discontinuity in delivering contrast agent may also adversely impact the quality of the imaging procedure by delaying a critical infusion time. Furthermore, the attendant must monitor the contrast agent within the syringe barrel for detecting non-suspended contrast agent, and must then intervene to resuspend the sedimented agent. Manual manipulation to resuspend the contrast agent has the potential for contamination and/or human error, and may delay a critical point of the procedure, or even the entire procedure. The use of a magnetic stirrer introduces an additional component that must be sterilized and introduced into the syringe barrel, and requires a magnetic stir plate. A modification to a conventional power injector necessitates additional hardware, introduces an additional level of mechanical complexity, consumes space, and may not adhere to current syringe size standards.

Thus, an apparatus that is convenient to use, maintain, and store, and that results in maintenance and injection of an agent suspended within a suspending medium for at least the duration of an infusion procedure, and a method of using such an apparatus, is needed.

SUMMARY OF THE INVENTION

The present invention provides these and other features. The invention is directed to apparatus and methods for suspending an agent in a suspending medium within a container, rotating the container to maintain the suspension for extended periods, and selectively delivering the agent while suspended from the container. Further, the present invention provides apparatus and methods that permit the providing of agent to be paused or interrupted while continuing to maintain the suspension of the agent. An example of such a suspended agent is a contrast agent suspended in a suspending medium of a pharmaceutically-acceptable liquid.

An embodiment of the apparatus includes a rotary drive assembly operably connected to a container and an actuator drive assembly operably coupling the rotary drive assembly to an actuator of the container. The rotary drive assembly rotates the container about an axis of the rotary drive assembly so that the agent achieves and maintains a suspended state within the container. The actuator drive assembly transfers a force from the rotary drive assembly to the actuator of the container for operating the actuator to provide the agent in a suspended state from the container.

In one embodiment, the rotary drive assembly has a holder for the container coupled the container, and a motor that rotates the holder about the axis of the rotary drive assembly. As the motor rotates the holder, the container rotates in a planetary fashion about the axis. The holder may extend radially outward from the container so that the rotation is a planetary rotation. In one aspect, the rotary drive may include a threaded spindle with a first portion that is operably connected to the motor for rotation, and a second portion that is connected to the holder. The actuator drive assembly may include a coupling member for operating the actuator of the container, and may also include a clutch assembly that can releasably engage the coupling member with the spindle. For dispensing the suspended agent, a connector, such as a catheter, may be provided between the container and a patient. The apparatus may further include a switch to halt the actuating and rotary drive assemblies.

An alternative embodiment of the apparatus has a housing that encloses the container, an inner member that hold the container, and a motor oprerably coupled with the inner member for rotation of the inner member. The motor rotates the inner member relative to an axis of the housing to maintain the agent in suspension within the suspending medium. The rotation of the inner member also operates the actuator of the container for providing agent in suspension from the container.

An embodiment of the method comprises rotating the container about an axis of rotation sufficient to suspend the agent and delivering the agent from the container by exerting a force upon the actuator sufficient to operate the actuator as the container is rotating to maintain the agent in suspension. The rotating and the delivering may occur simultaneously or the rotating may occur before the delivering. Alternatively, the delivering may be interrupted while maintaining the rotating. In certain embodiments, the container may be rotated in a planetary orbit about the axis of rotation. In other embodiments, the container axis and the axis of rotation are collinear. The container may be prefilled with the agent, such as a contrast agent.

The design of the present invention is lighter, smaller, and relatively inexpensive to manufacture and use, compared with other alternatives such as a dedicated infusion pump that has been modified to achieve adequate mixing. In contrast to a modified power injector, the present invention can accommodate syringes of standard sizes.

Thus, the apparatus and method provide and maintain a homogeneous suspension of an agent, such as a contrast agent, in a suspending medium. This is valuable for extending the duration over which the contrast agent may be efficaciously injected for imaging enhancement. The apparatus is mechanically simple for reliable operation with infrequent maintenance, resulting in minimal non-operational time or downtime, and is compact for flexible positioning in a procedure room. These and other objectives, advantages, features, and embodiments will be apparent with reference to the following drawings and detailed description.

BRIEF DESCRIPTION OF THE DRAWINGS

FIG. 1 is a schematic side view of an apparatus for dispensing a suspended agent according to the present invention.

FIG. 2 is a perspective view of an alternative embodiment of an apparatus for dispensing a suspended agent according to the present invention.

FIG. 3A is a side, partially in cross section, view of the apparatus of FIG. 2.

FIG. 3B is a side, partially in cross section, view of the apparatus of FIG. 2, with the plunger extended.

FIG. 4 is an enlarged view of encircled area 4 of FIG. 3B.

DETAILED DESCRIPTION OF THE INVENTION

A device and method for dispensing a agent suspended in a suspending medium and maintaining a suspension of the agent for a duration consistent with an infusion is disclosed. The invention can be used to administer agents either by infusion or by bolus injection. As used herein, the term infusion connotes injection of an agent from a container into a patient at a slower rate and over a longer time period, in comparison to a bolus injection in which the entire contents of a container are injected into a patient at a relatively rapid rate and over a shorter time period. The inventive device permits the rate at which the agent is dispensed from its associated container to be modified, for example, to be slowed, accelerated, paused, interrupted, terminated, etc., while maintaining the agent in a suspended state.

FIG. 1 is a schematic view of one embodiment of an apparatus 50 in accordance with the present invention for providing a suspended agent such as a contrast agent from a container such as a syringe. The suspension could be provided to the container from a bulk container, as described in co-pending U.S. Pat. application Ser. No. 09/316,315, which is expressly incorporated by reference herein in its entirety. Alternatively, a syringe could be filled manually using aseptic techniques, or a prefilled syringe could be employed.

Referring to FIG. 1, a syringe 20, as is known to one of ordinary skill in the art, includes a barrel 22 with a flanged proximal end 24 and a distal end 26. Barrel 22 has a substantially uniform diameter and extends longitudinally to enclose a reservoir 28 that contains an agent 29 to be dispensed, such as a contrast agent. Proximal end 24 may be open for filling the reservoir 28, but in use receives a plunger 30 adapted to engage the interior of barrel 22 in a sliding fluid-tight fit. Plunger 30 is moveable along the longitudinal axis of barrel 22. Distal end 26 attaches for fluid communication with an outflow port 32 within a cannula 34. When a linear force of a sufficient magnitude is applied to plunger 30 in a proximal-to-distal direction, the agent 29 will be dispensed from reservoir 28 through an outflow port 32. The capacity of syringe 20 may be variable and may hold, for example, a maximum volume of 1 ml, 5 ml, 10 ml, etc. depending on the amount of agent 29 to be infused.

In one embodiment of the present invention, the exterior of cannula 34 carries a fitting (not shown) for releasable fluid-tight attachment to a complementary fitting carried by one end of a Luer lock connector 35. Luer lock connector 35 comprises a stationary coupling 36 joined to a rotatable coupling 38 by an intervening mating member 37. One Luer connector 35 suitable for this purpose is the model S-370016 manufactured by B. Braun Medical, Ltd. (Sheffield, England), a member of B. Braun Melsungen, A G. Stationary coupling 36 has a fitting that is adapted to attach to the fitting flange carried by cannula 34. Stationary coupling 36 and rotatable coupling 38 are configured to direct the agent 29 dispensed through outflow port 32 along the axial length of Luer lock connector 35. Mating member 37 carries a dynamic sealing member (not shown) that maintains a fluid-tight seal while permitting rotation. One end of a conduit 40 is releasably connected for fluid communication with stationary coupling 36. Conduit 40 delivers the homogeneously suspended agent 29 to a patient and may be, for example, an angiocatheter.

As shown in FIG. 1, apparatus 50 in accordance with the present invention includes a rotary drive assembly 51 and an actuator drive assembly 53. Rotary drive assembly 51 comprises a coupling member or holder 52 mounted to a threaded spindle 54 and a motor 60 operably connected to spindle 54. Actuator drive assembly 53 comprises a force-exerting member or pressure plate 58 and a clutch assembly 56 which permits selective engagement of plate 58.

Holder 52 extends radially outward from threaded spindle 54 and comprises a double yoke structure having a syringe mount 62 and a spindle mount 64 arranged in a spaced relationship. Syringe mount 62 is adapted to affix syringe to holder 52. In the specific embodiment shown in FIG. 1, syringe mount 62 comprises an opening with a cross-sectional profile dimensioned to slidably receive syringe 20 so that the flange of flanged proximal end 24 of syringe 20 abuts a surface of holder 52. A fastener 66 applies a radially inward force of contact that presses barrel 22 against the interior of syringe mount 62. When transversely secured by fastener 66, syringe 20 is constrained so that it cannot move parallel to its longitudinal axis. Spindle mount 64 is adapted to affix threaded spindle 54 to holder 52. In the specific embodiment shown in FIG. 1, spindle mount 64 comprises an opening with a cross-sectional profile dimensioned to receive threaded spindle 54. A fastener 68 applies a radially inward force of contact that presses threaded spindle 64 against the interior of spindle mount 64. Holder 52 also includes a switch 69 that is adapted, when actuated, to selectively deenergize motor 60.

Motor 60 is mounted in a housing 73 (shown in phantom) and is operably connected to threaded spindle 54. When motor 60 is energized, threaded spindle 54 rotates about a longitudinal axis, in the direction shown by arrow 67, at a predetermined angular velocity. Motor 60 is attached to threaded spindle 54 by a mechanical linkage (not shown), for example, by intermeshed gears in a gear box, a planetary gear, or a belt. It will be understood that motor 60 may directly drive spindle 54 without departing from the spirit or scope of the present invention. Threaded spindle 54 comprises an elongate, cylindrical member having a continuously helical external thread 70 circumferentially disposed along a substantial length of its outer peripheral surface. In one embodiment, threaded spindle 54 is about 5 cm long and has 32 threads per inch, producing about 0.12 mm of linear travel per 360° revolution and a 36 ml/hr delivery rate. It is understood that the pitch of the thread 70 could be modified to produce either a slower delivery rate or a faster delivery rate for a given angular velocity of spindle 54 without departing from the spirit and scope of the present invention.

Pressure plate 58 is rotatably carried by a bearing 71 on threaded spindle 54. In the embodiment shown in FIG. 1, pressure plate 58 comprises a thin, circular plate with opposed parallel surfaces 72, 72a. Pressure plate 58 is configured so that a portion of surface 72 continuously contacts an actuator such as plunger 30 as threaded spindle 54 rotates. It will be appreciated that the configuration of pressure plate 58 may be changed without departing from the scope and spirit of the present invention. Examples of such changes in pressure plate 58 include, but are not limited to, a rod, a bar, a lever, and the like. A support arm 75 extends to a fixed attachment so that pressure plate 58 will remain stationary and cannot rotate in sympathy with spindle 54.

Clutch assembly 56 is carried by surface 72A and is adapted to releasably engage the external thread 70 of threaded spindle 54. In the embodiment depicted in FIG. 1, clutch assembly 56 comprises two sliding catches 76, 76A slideably fastened to surface 72A. If the catches 76, 76A are engaged with external thread 70, the rotation of threaded spindle 54 is converted by the helical revolution of clutch assembly 56 into a linear driving force that is applied to pressure plate 58. Pressure plate 58 further transmits the linear driving force to an actuator such as plunger 30 so as to incrementally advance plunger 30 toward distal end 26 of syringe 20. As plunger 30 advances, the agent 29 in reservoir 28 will be dispensed through outflow port 32. In an alternative embodiment, clutch assembly 56 may comprise a fastener, such as a nut, that is threadingly received by threaded spindle 54 and that is releasably engageable in a nonrotatable fashion with thread 70 of threaded spindle 54.

To conduct a dispensing operation, apparatus 50 is oriented such that the longitudinal axis of barrel 22 is approximately normal to the direction of gravitational forces so that the agent 29 will not longitudinally segregate in the suspending medium to either of the proximal end 24 or the distal end 26 of syringe 20. However, it is appreciated by those of ordinary skill in the art that the longitudinal axis of barrel 22 may have a slight inclination angle if the rate of longitudinal movement of the agent 29 is negligible over the duration of the dispensing operation. Generally, the permissible inclination angle will depend upon the viscosity of the suspending medium and the buoyancy of the agent 29.

Motor 60 is energized to rotate syringe 20 in a planetary orbit about the longitudinal axis of threaded spindle 54. A typical angular velocity or rotation rate for threaded spindle 54 is about 3 revolutions per minute (rpm) to about 30 rpm. A typical time required to suspend agent 29 from a non-suspended state to a suspended state is about one minute to about five minutes depending upon the rotation rate. After the agent 29 is determined to be suspended in reservoir 28 by visual means or another method, clutch assembly 56 is engaged so that pressure plate 58 advances in a proximal-to-distal direction while surface 72 contacts plunger 30. As a result, a linear driving force provided by motor 60 moves plunger 30 in a proximal-to-distal direction with a linear velocity proportional to the angular velocity of threaded spindle 54. As plunger 30 advances toward proximal end 26 of barrel 22, suspended agent 29 will be provided from reservoir 28 through outflow port 32, traverse the passageway in Luer connector 35, and enter the interior of conduit 40 for delivery into the vasculature of a patient about to undergo, or in the process of undergoing, an imaging procedure. For a 3 ml syringe, the delivery rate may range from about 5 ml/hr to about 50 ml/hr, depending upon the rotation rate of spindle 54 and the speed of motor 60. Because conduit 34 is attached to rotating portion 36 of Luer lock connector 35, conduit 40 will not rotate as syringe 20 is revolved in its planetary orbit about threaded spindle 54.

If administration of agent 29 must be discontinued or interrupted, the agent 29 may be maintained in suspension in the syringe by disengaging clutch assembly 56 so as to halt the advance of pressure plate 58. If pressure plate 58 is stationary, plunger 30 will no longer advance toward distal end 26 of syringe 20 and the delivery of the agent 29 will cease. However, syringe 20 will continue to revolve in its planetary orbit about threaded spindle 54 unless motor 60 is purposefully deenergized. As a result, the suspension will persist until administration of agent 29 is reinitiated or completed.

Figure 2:
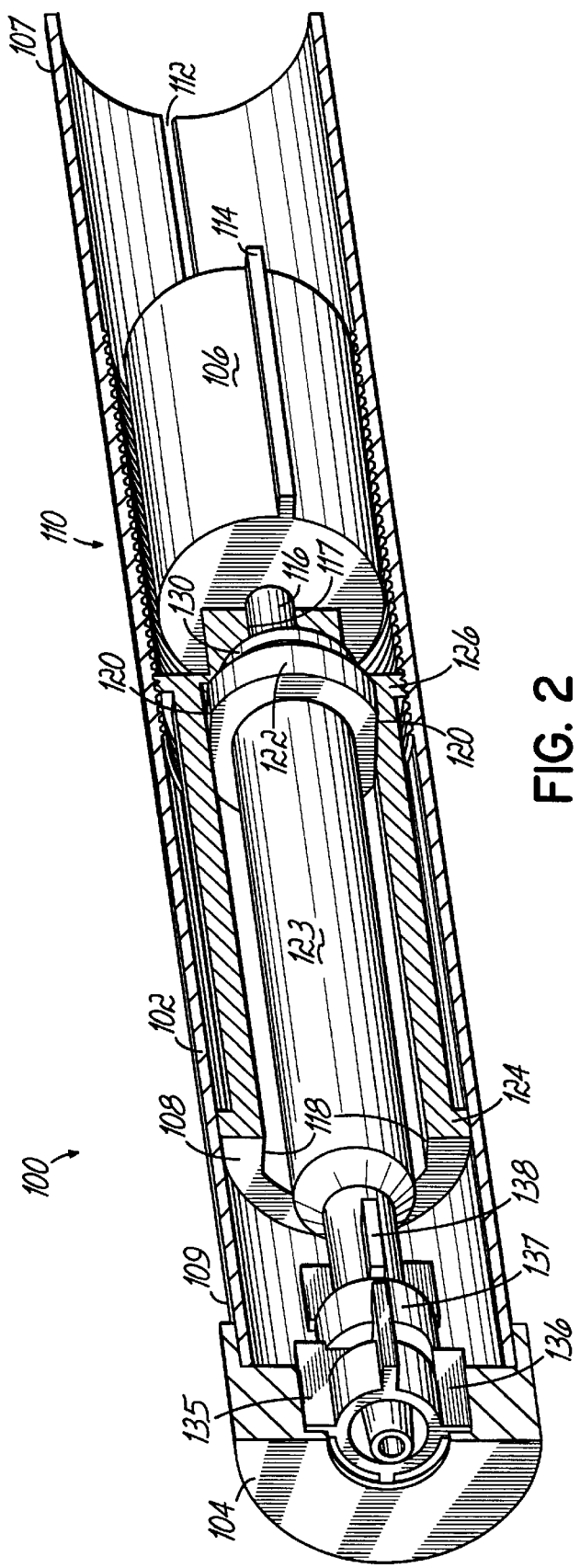

An alternative embodiment of an apparatus 100, according to the principles of the present invention, is shown in FIGS. 2–4. With reference to Figs. FIGS. 2, 3B and 4, a syringe 123 contains agent 129 to be delivered, wherein the agent 129 is dispersed in a suspending medium. With reference to FIG. 3A, syringe 123 has been substantially emptied of its contents.

Referring to FIG. 2, apparatus 100 includes an outer case or housing 102, a motor 106 positioned within housing 102, and a tumbler 108 operably linked to motor 106. Housing 102 includes a cylindrical wall that extends along a longitudinal axis from a proximal end 107 to a distal end 109. Distal end 109 is covered by a removable cover 104. The cover 104 is removable for inserting syringe 123, either filled or empty, into the interior of housing 102. A threaded portion 110 is provided along a length of an interior surface of housing 102 with one or more longitudinal slots 112 on the proximal end 107 of housing 102. The exterior of motor 106 carries a flange 114 that is configured and positioned to be slideably received within the respective slot 112. The engagement between flange 114 and slot 112 inhibits motor 106 from rotating about the longitudinal axis of the motor 106 with respect to housing 102. As motor 106 moves longitudinally within housing 102, each flange 114 rides within its respective slot 112. Motor 106 may be reversible and may be powered by a DC power source such as batteries, a spring-loaded wind-up mechanism, an AC power source, or an alternative power source as is known to one of ordinary skill in the art.

Motor 106 is configured to rotate a drive shaft 116 that extends into a recess 117 provided in tumbler 108. Drive shaft 116 is secured within the recess 117 by a set screw (not shown) or another fastening method known in the art. Tumbler 108 is an annular cylindrical elongate structure with centering flanges 124 and 126 extending radially outwardly from the outer surface of tumbler 108 at opposed ends thereof. Flanges 124, 126 serve to center tumbler 108 within housing 102. Flange 126 includes a threaded portion, as shown in FIG. 4, on an exterior housing-contacting surface that is positioned and configured to engage threaded portion 110 of the housing 102. The interior of tumbler 108 includes flats 118 that are positioned and configured to engage corresponding flats 120 carried by flange 122 of syringe 123.

The interior and exterior dimensions of tumbler 108 can be varied to accommodate syringes 123 of varying capacity, as well as to fit within the interior of housing 102. It will be understood that the interior dimensions of either tumbler 108 or housing 102 may be varied without departing from the spirit and scope of the present invention. Because the internal surfaces of tumbler 108 and housing 102 are in contact with the exterior of syringe 123, the sterility of the procedure is maintained.

A Luer connector 135 is attached to the distal end of syringe 123 and in fluid communication with the interior of syringe 123. A stationary coupling 136 of Luer connector 135 cannot rotate due to an abutting engagement with an interior portion of removable cover 104. When motor 106 is energized, tumbler 108 simultaneously rotates syringe 123 and advances the plunger 130 to provide a dispensing force to dispense the contents of syringe 123. Because the stationary coupling 136 is not free to rotate, the attached conduit (not shown) will remain rotationally stationary.

To prepare apparatus 100 for a dispensing operation, the removable cover 104 is removed from the end of housing 102. A syringe 123, which may be prefilled with a suspended agent 129, is positioned within the interior of tumbler 108 as shown in FIG. 4A. Alternatively, an empty syringe 123 may be positioned within the tumbler 108 and filled by placing the distal end of syringe 123 in fluid contact with a quantity of agent 129 and aspirating the plunger 130. The syringe 123 is inserted so that the flats 120 on the syringe body engage the corresponding flats 118 within the interior of tumbler 108. The proximal end of plunger 130 abuts the proximal portion of tumbler 108. After inserting syringe 123, the Luer connector 135 is attached to the distal end of syringe 123. Removable cover 104 is refitted on distal end 109 of the housing 102 and engages stationary coupling 136. An appropriate conduit (not shown) such as an angiocatheter is attached to the end of Luer connector 135.

Apparatus 100 is oriented such that the longitudinal axis of syringe 123 is approximately normal to the direction of gravitational forces so that the suspended agent 129 will not longitudinally segregate in the suspending medium to either of the opposite ends of syringe 123. However, it is appreciated by those of ordinary skill in the art that the longitudinal axis of syringe 123 may have a slight inclination angle if the rate of longitudinal movement of the agent 129 is negligible over the duration of the dispensing operation. Generally, the permissible inclination angle will depend upon the viscosity of the suspending medium and the buoyancy of the agent 129. To initiate the motor 106 is energized with a specific angular velocity, which is imparted by the securement of drive shaft 116 in recess 117 to tumbler 108. As tumbler 108 rotates about the longitudinal axis of housing 102, the meshing of the threaded portion of the case 110 and the threads on the periphery of centering flange 126 constrains the tumbler 108 to rotate helically. As tumbler 108 advances towards the distal end 109 of syringe 123, the engagement between the proximal portion of tumbler 108 and plunger 130 advances plunger 130 within the interior of syringe 123. As the plunger 130 advances toward distal end 109, suspended agent 129 within syringe 123 in provided through the lumen in Luer connector 135 and into the attached conduit (not shown). The helical, unidirectional rotation of syringe 123 establishes and maintains a uniform suspension of the suspended agent 129 within the interior of syringe 123. Because the rotation and delivery are simultaneous, the suspended agent 129 is maintained in a suspended state throughout an imaging, whether agent is infused or injected.

For imaging using energy from ultrasound waves (ultrasonic imaging), one type of contrast agent consists of gas-filled microspheres in a pharmaceutically-acceptable suspending carrier medium. Since gases have a greatly enhanced echogenicity compared with liquids or solids, the gas-filled microspheres strongly reflect sound waves. Microspheres are buoyant within the carrier medium so that a homogenous suspension is difficult to attain and maintain for an extended duration of administration. The device and method of the invention may be used to remedy this problem, as illustrated in the following example.

EXAMPLE

A 3 ml glass syringe was filled with a microsphere-containing contrast agent, specifically Optison®. Optison® is an aqueous suspension of albumin microspheres containing perfluoropropane ($C_3F_8$).

After inverting the syringe to expel excess gas, the syringe was placed into the holder of the apparatus shown in FIG. 1 and in accordance with the principles of the present invention. The pressure plate was brought into contact with the end of the plunger and the clutch assembly was disengaged. In this example, the threaded spindle was a number 10 screw having 32 threads per inch. The distal end of the syringe was equipped with a Luer rotating adapter (manufactured by B. Braun) and a 19-gauge angiocatheter, so as to simulate an actual infusion setup.

While the angiocatheter was held stationary, a motor/gearbox combination (a Fischer Scientific SL300 stirrer unit) was energized so as to rotate the threaded spindle and move the syringe in its planetary orbit. In this example, the syringe was rotated with an angular velocity of about 15 revolutions per minute.

After rotating the syringe for approximately two minutes, the microspheres were sufficiently homogeneously dispersed in the pharmaceutical carrier liquid to create a homogeneous suspension. At that point, the clutch was engaged to advance the plunger within the barrel of the syringe. Agent dispensed from the angiocatheter port was collected in aliquots for subsequent analysis of microsphere distribution. Dispensing of agent was continued until the syringe was emptied. The total travel distance of the plunger in the syringe was about two inches, i.e., 72 turns of the screw. Hence, the syringe was emptied in slightly less than five min, which is a reasonable time for imaging an organ such as a heart with ultrasound.

Aliquots (500 $\mu$l) of agent were collected from the open end of an angiocatheter connected to the syringe assembly. Each aliquot was analyzed for microsphere size and concentration using a Coulter particle size analyzer (Beckman Coulter, Inc., Fullerton, Calif.).

Generally, Coulter particle size analysis occurs as particles suspended in an electrolyte solution pass through a small aperture between electrodes that forms a sensing zone. In the sensing zone, each particle displaces its own volume of electrolyte. Volume displaced is measured as a voltage pulse, the height of each pulse being proportional to the volume of the particle. The volume agent drawn through the aperture is precisely controlled to allow the system to count and size particles for an accurate and reproducible volume independent of particle shape, color and density.

A standard set of conditions for the Coulter method of sizing and counting suspended particles was chosen: a 50-$\mu$m aperture, 200 ml of electrolyte, in this case isoton® buffer, a 500 $\mu$l aliquot volume of agent, and a 20 $\mu$l injection volume. The results were as follows:

| Aliquot (about 1 min each) | Mean particle size ($\mu$m) | Particle concentration ($\times 10^6$/ml) |
| --- | --- | --- |
| 1 | 3.315 | 1003 |
| 2 | 3.328 | 969 |
| 3 | 3.323 | 945 |
| 4 | 3.265 | 1004 |
| 5 | 3.286 | 1051 |

Over the entire dispensing period, the mean size and particle concentration of agent was approximately equivalent in each of the five aliquots. From a statistical analysis of the five aliquots, the average and standard deviation of the mean particle size was calculated to be 3.303 $\mu$m±0.027 $\mu$m, and the average and standard deviation of the particle concentration was calculated to be 994×10$^6$/ml±40×10$^6$/ml.

The previously described details, aspects and embodiments of the present invention present many advantages. An apparatus according to the principles of the present invention homogeneously suspends an agent, such as a contrast agent, for the duration of an imaging procedure, so that a uniform suspension of agent is infused into a patient. In addition, the apparatus is lighter, smaller, and relatively inexpensive to manufacture and use compared with a dedicated power injector that has been modified for mixing.

It should be understood that the embodiments of the present invention shown and described in the specification are only preferred embodiments of the inventor who is skilled in the art and are not limiting in any way. For example, the inventive apparatus and method may be used in conjunction with a container, such as the container or delivery device described in co-pending U.S. patent application Ser. No. 09/316,315. Therefore, various changes, modifications or alterations to these embodiments may be made or resorted to without departing from the spirit of the invention and the scope of the following claims.

What is claimed is:

1. An apparatus for providing a suspended agent from a container having an actuator for providing the suspended agent from the container, comprising:

a rotary drive assembly having an axis, said rotary drive assembly operably connected to the container for rotating the container about said axis of the rotary drive; and an actuator drive assembly operably connected to the rotary drive assembly for transferring a force from said rotary drive assembly to the actuator of the container sufficient to operate the actuator as the container is rotated.

2. The apparatus of claim 1 further comprising a connector for conveying the suspended agent from the container to a patient.

3. The apparatus of claim 1 wherein said rotary drive assembly comprises:

a holder attached to the container; and a motor operably coupled to said holder for rotation of the container about said axis concurrently with rotation of said holder.

4. The apparatus of claim 3 wherein said holder extends radially outward from the container and the container rotates in a planetary orbit about said axis.

5. The apparatus of claim 3 further comprising a threaded spindle having a first portion that is operably connected to said motor and a second portion that is connected to said holder, said spindle having a longitudinal axis and being configured to rotate about the longitudinal axis of the spindle.

6. The apparatus of claim 5 wherein said actuator drive assembly comprises a coupling member mounted on said threaded spindle, said coupling member adapted to operate the actuator of the container.

7. The apparatus of claim 6 wherein the actuator drive assembly further comprises a clutch assembly adapted to releasably engage said coupling member with said threaded spindle for selectively exerting a dispensing force to operate the actuator.

8. The apparatus of claim 1 wherein said actuator drive assembly comprises a clutch assembly positionable to selectively exert a force to operate the actuator.

9. The apparatus of claim 1 further comprising a switch for de-energizing the rotary drive assembly and the actuator drive assembly.

10. An apparatus for maintaining an agent in suspension, wherein the agent is held in a container having an axis and an actuator, the apparatus comprising:
    means for rotating the container about the axis, said rotating means selectively providing a dispensing force; and
    means for providing the suspended agent from the container and operably connected to said rotating means, wherein said providing means is coverable of transferring the dispensing force from the rotating means to the actuator.

11. The apparatus of claim 10 wherein the providing means delivers the suspended agent from the container while the container is rotated by the rotating means.

12. An apparatus for maintaining an agent contained in a syringe in suspension the syringe having an axis and comprising a barrel holding the agent and a plunger mounted in the barrel, comprising:
    a threaded spindle having an axis;
    a rotary motor operably connected to said threaded spindle for rotating said spindle about one of the axis of the syringe or the axis of the spindle;
    a holder having a first portion attached to the syringe and a second portion extending away from the syringe to attach to the threaded spindle; and
    a force-exerting member mounted on said spindle, said force-exerting member configured to selectively exert a force upon the plunger sufficient to advance the plunger during rotation of the syringe for providing agent from the syringe while the agent is maintained in suspension.

13. The apparatus of claim 12 further comprising a clutch assembly adapted to selectively engage said force-exerting member with said spindle.

14. An apparatus for maintaining an agent contained in a container in suspension, wherein the container has an actuator operable for providing the agent from the container, the apparatus comprising:
    a housing for the container having a cylindrical wall and an axis;
    an inner member positioned within the interior of said cylindrical wall and configured to receive and hold the container, said inner member adapted to rotatably move about said axis of said housing; and
    a motor operably coupled to said inner member for rotation of the inner member, wherein said inner member is operably coupled to the actuator of the container for providing the agent from the container and the agent in the container is maintained in suspension by the rotation of the inner member.

15. The apparatus of claim 14 wherein said cylindrical wall of said housing has a threaded interior portion and said inner member includes a threaded peripheral portion for engaging said threaded interior portion of said cylindrical wall, wherein said engagement between the threaded portions permits rotation of said inner member relative to the axis of the housing.

16. The apparatus of claim 14 wherein said inner member has a first flange extending radially outward from a surface of said inner member, said first flange adapted to engage said cylindrical wall of said housing for rotatable motion.

17. The apparatus of claim 16 wherein said wall has a threaded interior portion and said first flange includes a threaded peripheral portion for engaging said threaded interior portion of said cylindrical wall of said housing.

18. The apparatus of claim 14, wherein said housing includes at least one open end and a cover removably mounted to said open end.

19. The apparatus of claim 18, wherein said cover having an opening to permit attachment of a connector to the container.

20. The apparatus of claim 19, wherein the connector has a first portion held stationary by said cover coupled in a fluid-tight manner to a second rotatable portion attached for rotation to the container.

21. A method for maintaining an agent in suspension, wherein the agent is in a container having an actuator and a container axis, said method comprising;
    rotating the container about an axis of rotation sufficient to suspend the agent; and
    delivering the agent from the container by exerting a force upon the actuator sufficient to operate the actuator as the container is rotating to maintain the agent in suspension.

22. The method of claim 21 wherein the rotating and the delivering occur simultaneously.

23. The method of claim 21 wherein the rotating occurs before the delivering.

24. The method of claim 21 further comprising interrupting the delivering and maintaining the rotating.

25. The method of claim 21 wherein the rotating comprises rotating the container in a planetary orbit about the axis of rotation.

26. The method of claim 21 wherein the container axis and the axis of rotation are collinear.

27. The method of claim 21 further comprising, before the step of rotating, prefilling the container with the agent.

28. The method of claim 21 further comprising a container and an agent in a suspending medium within the container.

29. The method of claim 28 wherein the agent is a contrast agent.

30. The method of claim 28 wherein the container is a syringe.

* * * * *

UNITED STATES PATENT AND TRADEMARK OFFICE
CERTIFICATE OF CORRECTION

PATENT NO.    : 6,387,077 B1
DATED         : May 14, 2002
INVENTOR(S)   : Klibanov et al.

It is certified that error appears in the above-identified patent and that said Letters Patent is hereby corrected as shown below:

Column 1,
Line 14, "in a suspended state go long as" should be -- in a suspended state so long as --

Column 5,
Line 30, "to affix syringe to holder 52" should be -- to affix syringe 20 to holder 52 --
Line 44, "threaded spindle 64" should be -- threaded spindle 54 --

Column 8,
Line 50, "suspended agent 129 within syringe 123 in provided through" should be
-- suspended agent 129 within syringe 123 is provided through --

Column 9,
Line 57, "in this case isoton®" should be -- in this case Isoton® --

Column 10,
Line 44, "axis of the rotary drive; and" should be -- axis of the rotary drive assembly; and --
Lines 65-67, "said spindle having a longitudinal axis and being configured to rotate about the longitudinal axis of the spindle" should be -- said threaded spindle having a longitudinal axis and being configured to rotate about the longitudinal axis of the threaded spindle --

Column 11,
Line 31, "syringe in suspension the syringe having" should be -- syringe in suspension, the syringe having --
Lines 36-37, "said spindle about one of the axis of the syringe or the axis of the spindle;" should be -- said threaded spindle about one of the axis of the syringe or the axis of the threaded spindle; --
Line 41, "mounted on said spindle," should be -- mounted on said threaded spindle, --

UNITED STATES PATENT AND TRADEMARK OFFICE
CERTIFICATE OF CORRECTION

PATENT NO. : 6,387,077 B1
DATED : May 14, 2002
INVENTOR(S) : Klibanov et al.

It is certified that error appears in the above-identified patent and that said Letters Patent is hereby corrected as shown below:

Column 11 cont'd,
Line 48, "member with said spindle" should be -- member with said threaded spindle --

Signed and Sealed this

Seventeenth Day of December, 2002

JAMES E. ROGAN
*Director of the United States Patent and Trademark Office*